(12) United States Patent
Roberts et al.

(10) Patent No.: US 6,303,063 B1
(45) Date of Patent: *Oct. 16, 2001

(54) PROCESS OF MAKING A YARN

(75) Inventors: Ian Roberts, Pencaitland; David MacKenzie Hill, Berwick, both of (GB)

(73) Assignee: Peri-Dent Limited, Selkirkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/330,491

(22) Filed: Jun. 11, 1999

(51) Int. Cl.[7] .......................... A61C 15/04; D01D 5/088; D01D 5/098
(52) U.S. Cl. .................... 264/178 F; 264/210.5; 264/210.6; 264/210.7; 264/210.8; 264/211.12
(58) Field of Search ....................... 264/103, 178 F, 264/210.5, 210.6, 210.7, 210.8, 211.12

(56) References Cited

U.S. PATENT DOCUMENTS 3,800,812   4/1974  Jaffe .

FOREIGN PATENT DOCUMENTS

| 0 339 935 A | 11/1989 | (EP) . |
| 2 128 133 A | 4/1984 | (GB) . |
| 2 258 402 A | 2/1993 | (GB) . |

*Primary Examiner*—Leo B. Tentoni
(74) *Attorney, Agent, or Firm*—Adams, Schwartz & Evans, P.A.

(57) ABSTRACT

A method of converting a plastics material into a yarn includes heating the material to melt it and pumping the melted material through an extrusion die (114) to form an extruded filament (116). The extruded filament is cooled and passed through a first draw roller assembly (122) while elevating the temperature of the filament. The filament (116) is heated in a heating zone (126) as it exits the first draw roller assembly. Thereafter the filament is passed through a second draw roller assembly (134) operating at a different linear speed to the first draw roller assembly (122). The filament (116) is spooled after exiting the second draw roller assembly (134).

42 Claims, 3 Drawing Sheets

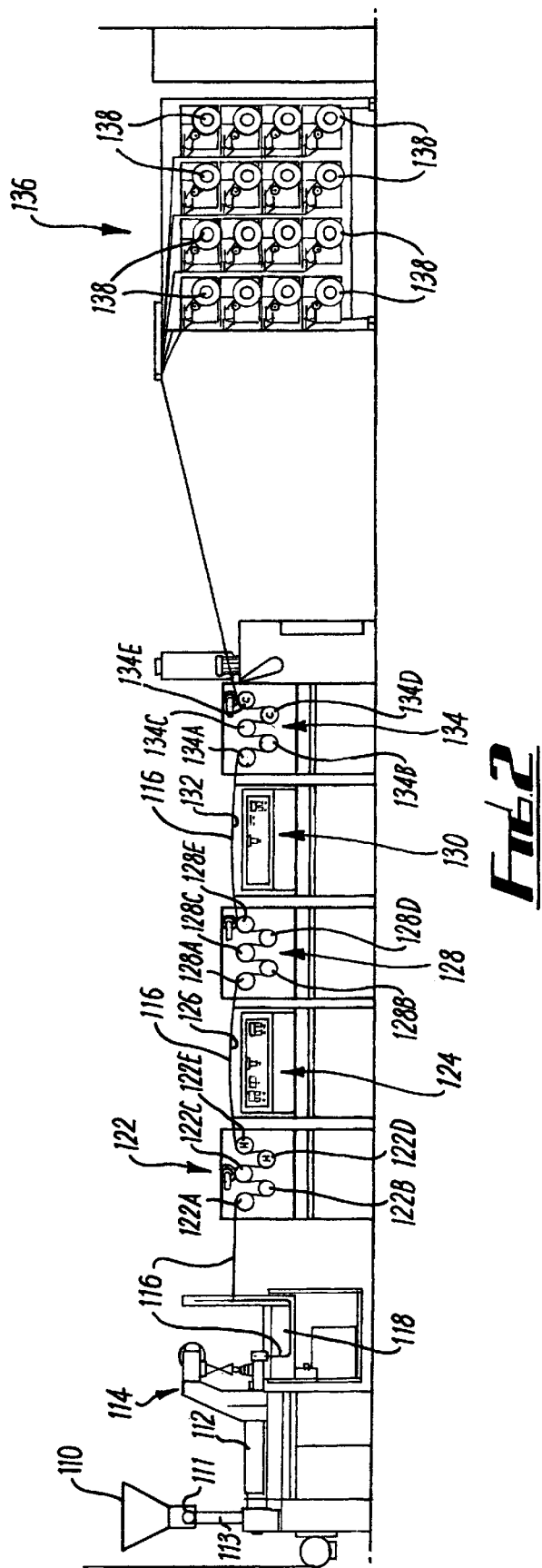

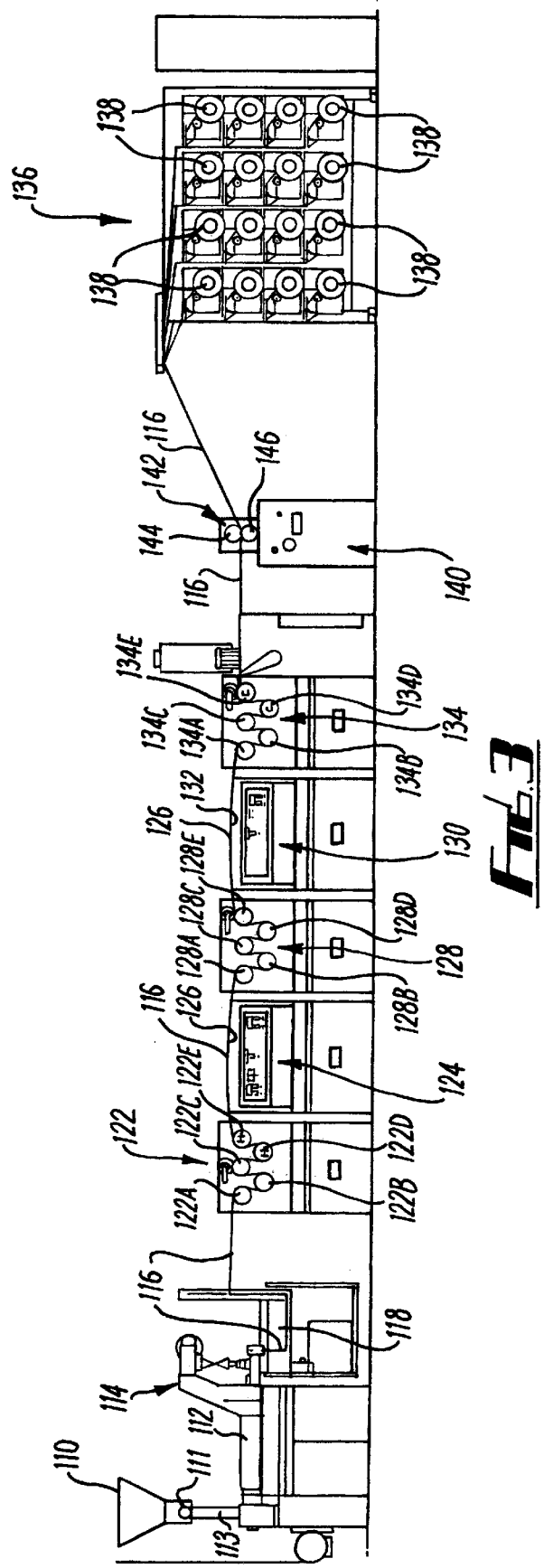

PROCESS OF MAKING A YARN

TECHNICAL FIELD AND BACKGROUND OF THE INVENTION

The present invention concerns an improved method for making a plastics material yarn and the yarn made by the method, especially but not exclusively, a method of manufacturing our yarn from polypropylene or polyethylene or a blend of these materials to provide a dental floss or tape.

Polytetrafluoroethylene (PTFE) has been recognised as a material which, in yarn form, gives satisfactory results in certain specialist applications, for example, dental floss or tape. PTFE is a relatively costly material and there is a desire to provide a yarn exhibiting the same overall characteristics as PTFE but being formed from a less expensive material.

SUMMARY OF THE INVENTION

According to one aspect of this invention there is provided a method of converting a plastics material into a yarn, comprising heating the plastics material to melt it, passing melted material through an extrusion die to form an extruded filament, and thereafter cooling the filament.

According to another aspect of the present invention there is provided a method of converting a plastics material into a yarn, comprising heating the material to melt it, pumping melted material through an extrusion die to form an extruded filament, cooling the extruded filament, passing the extruded filament through a first draw roller assembly while elevating the temperature of the filament, heating the filament in a heating zone as it exits from the first draw roller assembly and, thereafter, passing the filament through a second draw roller assembly operating at a different linear speed than the first draw roller assembly and spooling the filament exiting the second draw roller assembly.

The plastics material may comprise a polymeric plastics material, which may be selected from the group comprising polyalkenes. Suitably, the material comprises one or more polyalkenes formed from one or more of $C_2$–$C_3$ alkenes. Suitably, the plastics materials is polyethylene or polypropylene, a blend of polyethylene and polypropylene, or a co-polymer of ethylene and propylene. The plastics material may be provided in the form of granules.

Where the plastics material is a co-polymer of ethylene and propylene, the material may comprise from 0 to 100% wt/wt of said co-polymer, preferably from 0 to 60%, and more preferably from 0 to 40% of said co-polymer.

The material may further include polytetrafluoroethylene (PTFE), for example in an amount of 5 to 10% wt/wt.

The material may comprise a rubberising product comprising a propylene polymer with ethene. For example, a product sold under the trade mark ADFLEX can be used. Alternatively, any other similar such product can be used. The material may comprise from 0 to 100% wt/wt of said product, preferably from 0 to 60% wt/wt, more preferably, from 0 to 40% wt/wt. The use of the rubberising product has the effect of rendering to the yarn a more rubbery texture. This can be advantageous when the yarn is to be used as a dental floss.

The material may include an ethylene vinyl acetate polymer, which may be a co-polymer, the co-polymer including a vinyl acetate, preferably at 7 to 18% wt/wt. An example of a suitable such co-polymer is sold under the trade mark EVATANE by Elf Atochem UK Ltd.

The material may include from 0 to 100% wt/wt of said ethylene vinyl acetate polymer, preferably 0 to 60% wt/wt, more preferably 0 to 40% wt/wt.

Silica may be added to the plastics material. Preferably, the silica is added in the form of particles. Preferably, silica is added to the material in an amount of 1% to 5% wt/wt. The silica may be added to the material prior to or during heating thereof. The silica may be a coloured silica.

A silicone may be added to the material. The silicone may be linear polydimethyl silicone, suitably one sold by Dow Corning under the designation ME50-001 SILICONE MASTERBATCH. The silicone may be added in an amount 1–50% wt/wt, preferably 5–20% wt/wt, more preferably 10–15% wt/wt.

In the first embodiment, the rollers in the first heated draw roller assembly are rotating such as to impart to the filament a speed which may lie within the range 0–200 m per minute, preferably within the range 5 to 40 m per minute. More preferably it is 20 m per minute.

The temperature of the rollers in the first heated draw roller assembly of the first embodiment may lie within the range 0–200° C., preferably within the range 80 to 160° C. More preferably it is 95° C. The temperature in the heating zone at the exit from the first draw roller assembly may lie within the range 0–200° C., preferably within the range 80 to 140° C. More preferably it is 120° C.

Preferably the second draw roller assembly operates at a higher speed than the first draw roller assembly. In a first embodiment of the invention the second draw roller assembly is heated.

The temperature of the rollers in the second heated draw roller assembly of the first embodiment may lie within the range 0–200° C., preferably within the range 80 to 140° C. More preferably it is 90° C.

The rollers of the second heated draw roller assembly of the first embodiment are rotating such as to impart to the filament a speed which may lie within the range 0–1000 m per minute, preferably within the range 50 to 250 m per minute. More preferably it is 80 m per minute.

In a second embodiment, the filament may be passed through an intermediate draw roller assembly arranged downstream of the first draw roller assembly and upstream of the second draw roller assembly.

In the second embodiment the extruded filament may be further heated in a second heating zone as the filament exits the intermediate draw roller assembly. Conveniently, the filament is substantially not heated as it passes through the intermediate draw roller assembly.

In the second embodiment, the rollers in the first draw roller assembly are rotating such as to impart to the filament a speed which may lie within the range of 16–50 m per minute, conveniently substantially 32 m per minute.

Preferably, the first draw roller assembly of the second embodiment comprises a plurality of rollers, conveniently five. The temperature of at least one of the rollers in the first draw roller assembly of the second embodiment may lie in the range of 50–100° C., conveniently 96–100° C. Conveniently the roller of the first draw roller assembly arranged furthest downstream thereof is heated. Preferably, the roller immediately upstream of said furthest downstream roller is also heated.

The temperature of the first mentioned heating zone at the exit from the first draw roller assembly of the second embodiment may lie in the range of 100–135° C., conveniently 116–177° C.

The temperature of the second heating zone at the exit from the intermediate draw roller assembly may lie in the range of 100–150° C., conveniently substantially 150° C.

The intermediate draw roller assembly may comprise a plurality of rollers, conveniently five. The rollers in the intermediate draw roller assembly are rotating such as to impart to the filament a speed which may lie in the range 150–250 m per minute, conveniently substantially 175 m per minute.

The second draw roller assembly in the second embodiment may comprise a plurality of rollers, conveniently five. The rollers in the second draw roller assembly are rotating such as to impart to the filament a speed which may lie in the range 100–250 m per minute, conveniently substantially 160 m per minute, for example 158 m per minute.

The extruded filament may be cooled as it passes through the second draw roller assembly of the second embodiment. At least one of the rollers of the second draw roller assembly is at a temperature in the range 5–15° C., conveniently 11–12° C. Conveniently, the roller of the second draw roller assembly arranged furthest downstream thereof is cooled. Preferably, the roller immediately upstream of said furthest downstream roller is also cooled.

In one embodiment, flattering means is provided to flatten the filament. The flattening means may comprise at least one roller, and preferably a pair of flattening rollers between which the filament can pass. The flattening rollers are conveniently arranged to impart to the filament a thickness in the region of substantially 0.05–0.075 mm. Prior to passing through the flattening means the filament may have a thickness of substantially 0.095 mm.

Preferably, the flattening means acts to bilaterally orient the molecules in the filament, thereby providing improved lateral strength.

Preferably the filament is extruded in a generally downward direction from the extruder.

Preferably the extruded filament is cooled in a water bath. Preferably the temperature of the water in the bath is controlled.

Preferably the height of the water bath is adjustable to regulate the cross-section of the extruded filament.

Preferably the filament, as it leaves the extruder, takes the form of the extruding die which is generally rectangular in shape having radiused corners.

Preferably the dimensions of the extruder die are 12 mm×0.5 mm.

Preferably the granules are formed from polypropylene of a type known as 66/34LD. The flow rate of melted granules through the extruder may lie within the range 2–12 g per min.

The temperature of the melted granules may lie in the range 200–300° C., preferably within the range 250 to 290° C.

Preferably the extruder pressure lies within the range 600–1400 psi. Preferably it is 1000 psi. Preferably the speed of the metering pump feeding the molten granules to the extrusion die is 1–18 revs per minute, preferably 2 to 8 revs per minute. More preferably it is 6 revs per minute.

The water temperature within the cooling bath may be 5–50° C., preferably 10 to 40° C. More preferably it is 35° C.

The distance between the exit from the extrusion die and the water level in the cooling bath may lie within the range 2–40 mm, preferably 2 to 15 mm. More preferably it is 5 mm.

When a dental floss has to be formed, the distance between the extrusion die and the water level may lie within the range 2 to 15 mm. More preferably it is 5 mm. The depth of the water within the cooling bath may lie within the range 0.1 to 50 cm, preferably within the range 10 to 20 cm. More preferably it is 15 cm.

The speed of the spooling assembly may lie within the range 0–1000 m per minute, preferably within the range 50 to 250 m per minute. More preferably it is 80 m per minute.

According to another aspect of the present invention there is provided a polypropylene yarn manufactured in accordance with the method set out in any of the preceding twenty paragraphs.

In a first embodiment, the plastics material yarn may be manufactured by a method comprising heating to a temperature within the range 200–300° C. granules of a plastics material, preferably polypropylene plastics material, causing the melted granules to flow to an extrusion metering pump at a rate lying within the range 2–12 g per min, passing the melted material through the extrusion metering pump operating it at a speed within the range 1–18 revs per minute to create an extrusion pressure lying within the range 600–1400 psi, extruding the material through a die and guiding the extruded filament into a bath located between 2 and 40 mm below the exit from the extruder die and containing a cooling fluid, for example water, at a temperature lying within the range 5–50° C., passing extruded filament from the water bath to a first heated draw roller assembly where the rollers are heated to a temperature of between 0–200° C. and pass filament therethrough at a speed lying within the range 0–200 m per minute, heating the filament exiting from the first draw roller assembly in a heating zone to a temperature lying within the range 0–200° C. passing the material through a second heated draw roller assembly where the rollers are heated to a temperature of between 0–200° C. and passing the yarn therethrough at a speed of between 0–1000 m per minute and spooling filament exiting from the second heated draw roller assembly at a speed of between 0–1000 m per minute.

In a second embodiment, the plastics material yarn may be manufactured by a method comprising heating to a temperature within the range of 200–300° C. granules of a plastics material, preferably polypropylene plastics material, causing the melted granules to flow to an extrusion metering pump, passing the melted material through the pump and extruding the material through a die into a bath located between 2 and 40 mm below the exit of the extruder die and containing a cooling fluid, for example water at a temperature lying within the range of 5–50° C., passing the extruded filament from the bath to a first heated draw roller assembly where at least one of the rollers are heated to a temperature lying in the range of 50–100° C., and passing the filament therethrough at a speed lying within the range of 16–50 m per minute, heating the filament exiting from the first draw roller assembly in a first heating zone to a temperature lying in the range of 100–135° C., passing the filament through an intermediate draw roller assembly at a speed lying within the range of 150–250 m per minute, heating the filament exiting from the intermediate draw roller assembly in a second heating zone to a temperature lying in the range of 100–150° C., passing the filament through a second draw roller assembly where at least one of the rollers is cooled to a temperature lying in the range of 5–50° C., and spooling the filament exiting from the second draw roller assembly.

According to another aspect of the invention there is provided a plastics material yarn having a width in the range of 0.5–4 mm, and a decitex in the range of 500–1500.

Preferably, the tensile strength of the yarn is in the range of 12–30N, more preferably 15–25N. The width of the yarn may be in the range of 0.6 to 1.5 m. Suitably, the width is 0.6 mm, 1.1 mm or 1.5 mm. The decitex of the yarn may be in the range of 550–1000.

Preferably, the yarn comprises a polymeric plastics material, suitably one or more polyalkenes formed from one or more of $C_2$–$C_3$ alkenes. Suitably, the plastics material is polyethylene or polypropylene, a blend of polyethylene or polypropylene, or a co-polymer of ethylene and propylene.

Where the plastics material is a co-polymer of ethylene and propylene, the material may comprise from 0 to 100% of said co-polymer, preferably from 0 to 60%, and more preferably from 0 to 40% of said co-polymer.

The material may include PTFE, for example in an amount of 5 to 10% wt/wt.

The material may comprise a product comprising a propylene polymer with ethene. For example, a product sold under the trade mark ADFLEX can be used. Alternatively, any other similar such product can be used. The material may comprise from 0 to 100% wt/wt of said product, preferably from 0 to 60% wt/wt, more preferably from 0 to 40% wt/wt.

The material may include an ethyl vinyl acetate polymer, which may be a co-polymer, the co-polymer including a vinyl acetate, preferably at 7 to 18% wt/wt. An example of a suitable such co-polymer is sold under the trade mark EVATANE.

The material may include from 0 to 100% wt/wt of said ethylene vinyl acetate, preferably 0 to 60% wt/wt, more preferably 0 to 40% wt/wt.

The material may include silica, which may be in the form of particles. Preferably, the silica comprises 1 to 5% wt/wt of the material. The silica may be a coloured silica.

The material may include a colouring, for example Titanium dioxide. The material may include from 0 to 5% wt/wt of said colouring, preferably substantially 1% wt/wt.

According to another aspect of this invention there is provided apparatus for converting a plastics material into a yarn, the apparatus comprising means for melting the material, means for pumping melted material through an extrusion die to form an extruded filament, means for cooling the extruded filament, a first draw roller assembly to draw the extruded filament therethrough, heating means to heat at least one of the rollers of said first draw roller assembly, a heating zone arranged at the exit of the first draw roller assembly to heat the extruded filament exiting from said first draw roller assembly, a second draw roller assembly operating at a different linear speed to the first draw roller assembly, and spooling means for spooling the filament exiting from the second draw roller assembly.

In a first embodiment, the rollers in the first heated draw roller assembly are rotating such as to impart to the filament a speed which may lie within the range 0–200 m per minute, preferably within the range 5 to 40 m per minute. More preferably it is 20 m per minute.

The temperature of the rollers in the first heated draw roller assembly of the first embodiment may lie within the range 0–200° C., preferably within the range 80 to 160° C. More preferably it is 95° C. The temperature in the heating zone at the exit from the first draw roller assembly may lie within the range 0–200° C., preferably within the range 80 to 140° C. More preferably it is 120° C.

Preferably the second draw roller assembly operates at a higher speed than the first draw roller assembly. In the first embodiment of the invention the second draw roller assembly may be heated.

The temperature of the rollers in the second heated draw roller assembly of the first embodiment may lie within the range 0–200° C., preferably within the range 80 to 140° C. More preferably it is 90° C.

The rollers of the second heated draw roller assembly of the first embodiment are rotating such as to impart to the filament a speed which may lie within the range 0–1000 m per minute, preferably within the range 50 to 250 m per minute. More preferably it is 80 m per minute.

In a second embodiment, the apparatus may include an intermediate draw roller assembly arranged downstream of the first draw roller assembly and upstream of the second draw roller assembly.

In the second embodiment, the apparatus may include a second heating zone to heat the filament, the second heating zone being arranged at the exit of the intermediate draw roller assembly. Conveniently, intermediate draw roller assembly is not heated.

In the second embodiment, the rollers in the first draw roller assembly are rotating such as to impart to the filament a speed which may lie within the range of 16–50 m per minute, conveniently substantially 32 m per minute.

Preferably, the first draw roller assembly of the second embodiment comprises a plurality of rollers, conveniently five. The temperature of at least one of the rollers in the first draw roller assembly of the second embodiment may lie in the range of 50–100° C., conveniently 96–100° C. Conveniently the roller of the first draw roller assembly arranged furthest downstream thereof is heated. Preferably, the roller immediately upstream of said furthest downstream roller is also heated.

The temperature of the first mentioned heating zone at the exit from the first draw roller assembly of the second embodiment may lie in the range of 100–135° C., conveniently 116–177° C.

The temperature of the second heating zone at the exit from the intermediate draw roller assembly may lie in the range of 100–150° C., conveniently substantially 150° C.

The intermediate draw roller assembly may comprise a plurality of rollers, conveniently five. The rollers in the intermediate draw roller assembly are rotating such as to impart to the filament a speed which may lie in the range 150–250 m per minute, conveniently substantially 175 m per minute.

The second draw roller assembly in the second embodiment may comprise a plurality of rollers, conveniently five. The rollers in the second draw roller assembly are rotating such as to impart to the filament a speed which may lie in the range 100–250 m per minute, conveniently substantially 160 m per minute, for example 158 m per minute.

The second draw roller assembly of the second embodiment may be cooled. At least one of the rollers of the second draw roller assembly is at a temperature in the range 5–15° C., conveniently 11–12° C. Conveniently, the roller of the second draw roller assembly arranged furthest downstream thereof is cooled. Preferably, the roller immediately upstream of said furthest downstream roller is also cooled.

In one embodiment, flattening means is provided to flatten the filament. Preferably, the flattening means comprises at least one roller, and preferably a pair of flattening rollers between which the filament can pass. The flattening rollers are conveniently arranged to impart to the filament a thickness in the region of substantially 0.05 to substantially 0.075 mm. Prior to passing through the flattening means the filament may have a thickness of 0.095 mm.

Preferably, the flattening means acts to bilaterally orient the molecules in the filament, thereby providing improved laterial strength.

Preferably the filament is extruded in a generally downward direction from the extruder.

Preferably the cooling means is a water bath. Preferably the temperature of the water in the bath is controlled.

Preferably the height of the water bath is adjustable to regulate the cross-section of the extruded filament.

The flow rate of melted granules through the extruder may lie within the range 2–12 g per min.

The melting means may be adapted to heat the material to a temperature in the range 200–300° C., preferably within the range 250 to 290° C.

Preferably the extruder pressure lies within the range 600–1400 psi. Preferably it is 1000 psi. Preferably the speed of the metering pump feeding the molten granules to the extrusion die is 1–18 revs per minute, preferably 2 to 8 revs per minute. More preferably it is 6 revs per minute.

The water temperature within the cooling bath may be 5–50° C., preferably 10 to 40° C. More preferably it is 35° C.

The distance between the exit from the extrusion die and the water level in the cooling bath may lie within the range 2–40 mm, preferably 2 to 15 mm. More preferably it is 5 mm.

When a dental floss has to be formed, the distance between the extrusion die and the water level may lie within the range 2 to 15 mm. More preferably it is 5 mm. The depth of the water within the cooling bath may lie within the range 0.1 to 50 cm, preferably within the range 10 to 20 cm. More preferably it is 15 cm.

The speed of the spooling assembly may lie within the range 0–1000 m per minute, preferably within the range 50 to 250 m per minute. More preferably it is 80 m per minute.

BRIEF DESCRIPTION OF THE DRAWINGS

Embodiments of the present invention will now be described by way of example only with reference to the accompanying drawings in which:

FIG. 2 shows diagrammatically a second embodiment of an apparatus for manufacturing plastics material yarn; and FIG. 3 shows diagrammatically a third embodiment of an apparatus for manufacturing plastics material yarn.

DESCRIPTION OF THE PREFERRED EMBODIMENT AND BEST MODE

Figure 1:
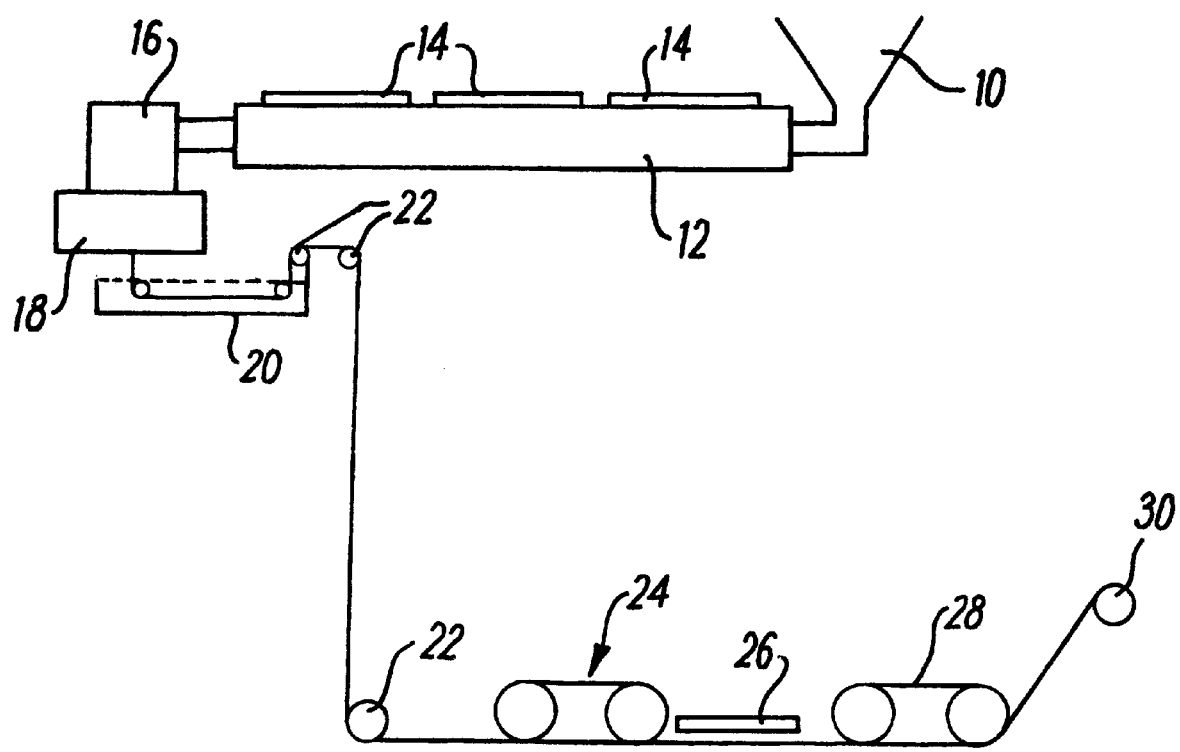
FIG. 1 shows diagrammatically a first embodiment of an apparatus for manufacturing plastics material yarn.

Referring to FIG. 1, there is shown a first embodiment of apparatus for manufacturing plastics material yarn, for example a dental floss or tape. The apparatus comprises a hopper 10 to which polypropylene granules of the type known as 66/34LD are supplied. Alternatively, a co-polymer of ethylene and propylene can be supplied to the hopper 10, or a blend of polyethylene and polypropylene.

Further ingredients can also be added at this stage to form a mixture. One of these further ingredients is polytetrafluoroethylene, which can be added in the form of granules, in an amount of 5 to 10% of the final mixture. A further component is an ethylene vinyl acetate polymer, which can suitably be an ethylene vinyl acetate/vinyl acetate co-polymer, containing 7 to 18% vinyl acetate. The ethylene vinyl acetate polymer or co-polymer can be added in the form of granules in an amount of 0 to 40% of the final mixture. A suitable such co-polymer is sold under the trade mark EVATANE by Elf Atochem UK Ltd.

A rubberising product or agent can be added, which can be a propylene polymer with ethylene. A suitable such ingredient is sold under the trade mark ADFLEX by Montell polyolefins. This product is added to improve the flexibility of the yarn. Preferably, the product is added in an amount of 0 to 40% wt/wt.

Silica particles can be added to the hopper 10 with the other ingredients. The silica can be added in an amount of 1 to 5% wt/wt. The silica can be coloured to provide the yarn with a mottled appearance. The silica has the effect, when the yarn is used as a dental floss or tape, of an abrasive to enhance the cleaning of the teeth.

A silicone may also be added. A suitable such silicone is one manufactured by Dow Corning under the designation MB50-001 SILICONE MASTERBATCH. The silicone may be added in an amount of 5–20% wt/wt. The silicone is provided in the form of pellets or granules.

The granules or the mixture are drawn into an extruder barrel 12 provided with heaters 14 and melted material from the extruder barrel 12 passes through a metering pump 16 feeding a diehead 18, the diehead providing an extrusion aperture of generally rectangular form having radius corners, the aperture being 8×0.06 mm with the axis of the extrusion aperture being in a generally vertical direction so that extruded filament leaves the die travelling in a downward direction.

The extruded filament is received in a water-filled cooling bath 20 and after passing therethrough it is guided by guide-rollers 22 into first heated draw roller assembly where the filament is heated and subjected to tension to extend it. Filament exiting from the first draw roller assembly 24 is re-heated under a hotplate 26 before passing into a second heated draw roller assembly where it is subjected to further tension and heat, the finally treated material being spooled on a spooling assembly 30.

With a propylene starting material known as 66/34LD the apparatus described above is operated under the following range of conditions:

| | |
|---|---|
| Resin Melt flow: | 2–12 g per minute |
| Melt Temp: | 200–300° C. |
| Extrusion Pressure: | 600–1400 psi |
| Metering Pump Speed: | 1–18 revs per mixture |
| Water Bath - Temp: | 5–50° C. |
| Die Height Above Water Level: | 2–40 mm |
| Water Depth. | 0.1–50 cm |
| Roller 1 Speed: | 0–200 meters per minute |
| Roller 1 Temp: | 0–200° C. |
| Hot Plate: | 0–200° C. |
| Roller2 Speed: | 0–1000 meters per minute |
| Roller 2 Temp: | 0–200° C. |
| Take Up Speed: | 0–1000 meters per minute |

In one specific example the apparatus is operated under the following conditions.

| | |
|---|---|
| Resin Melt flow: | MDI = 3.2 |
| Melt Temp: | 270° C. |
| Extrusion Pressure; | 1000 psi |
| Metering Pump Speed: | 6 revs per minute |

| | |
|---|---|
| Water Bath - Temp; | 35° C. |
| Die Height Above Water Level: | 5 mm |
| Water Depth: | 15 cm |
| Roller 1 Speed: | 20 meters per miuute |
| Roller 1 Temp; | 95° C. |
| Hot Plate: | 120° C. |
| Roller 2 Speed: | 80 meters per minute |
| Roller 2 Temp: | 90° C. |
| Take Up Speed: | 80 meters per minute (1% above roller 2 speed) |

The examples described above provide a polypropylene yarn in tape form which is suitable, if necessary after further treatment, for example, coating with wax with additives therein into a dental interproximal cleaning tape.

If a dental floss is required the same apparatus can be used but the water bath is lowered to a distance of between 4 and 8 mm from the exit from the extruder.

In a further modification polypropylene can be substituted with polyethylene the operating conditions lie within the following range.

| | |
|---|---|
| Resin Melt flow: | MFI 3.2 |
| Melt Temp: | 270° C. |
| Extrussion Pressure: | 1000 psi |
| Metering Pump Speed: | 3 revs per minute |
| Water Bath - Temp: | 35° C. |
| Die Height Above Water Level: | 5 mm |
| Water Depth: | 15 cm |
| Roller 1 Speed: | 20 meters per miuute |
| Roller 1 Temp: | 95° C. |
| Hot Plate: | 120° C. |
| Roller 2 Speed: | 80 meters per minute |
| Roller 2 Temp: | 90° C. |
| Take Up Speed: | 80 meters per minute |

In a still further modification a mixture of polypropylene and polyethylene may be employed.

Referring to FIG. 2 there is shown a second embodiment of apparatus for manufacturing plastics material yarn, for example a dental floss. The apparatus 10 comprises one or more feed hoppers 110 to feed one or more ingredients to a screw mixing barrel 112. The ingredients are suitably the same as those described for the first embodiment. If desired a white colouring material e.g. $TiO_2$ can be added in an amount of about 1% wt/wt. A separate hopper 110 is provided for each of the ingredients and the, or each, hopper 110 is provided with a screw feed 111 to feed a predetermined amount of the ingredient to the mixing barrel in at a predetermined rate. Between the hopper(s) 110 and the mixing barrel there is provided a vertical tube 113 known in the art to control the rate of feed of the material to the mixing barrel 12.

The mixing barrel 112 is heated to melt the material therein and the molten material is compressed in the barrel 112. The temperature inside the mixing barrel 112 is at about 250° C. A pump and die head assembly 114 is provided at the exit of the barrel 112 to pump the molten material through dies of appropriate shape to form a plurality of extruded filaments 116.

The filaments 116 are extruded downwardly into a cooling water bath 118 at a temperature of about 12° C. to cool the extruded filaments. The distance between the downwardly facing die apertures and the surface of the water bath 118 determines the width of filament passing through the bath 118.

The filaments 116 then pass over a plurality of guide rollers 120 to a first draw roller assembly 122 comprising five rollers 122A, B, C, D and E. The roller 122E which is furthest downstream of the rollers of the first draw roller assembly 122, and the roller 122D immediately upstream of the roller 122E, are heated to a temperature of about 96–100° C. The rollers of the first draw roller assembly 122 are rotating such as to impart to the filaments 116 a speed of about 32 m per minute, (for example 32.2 m per minute).

A first heating zone 124 is arranged adjacent, and downstream, of the first draw roller assembly 122. The first heating zone 124 comprises an upwardly convex heating plate 126 across which the filaments 116 pass. The heating plate 126 of the first heating zone 124 is heated to a temperature of about 116–117° C.

Downstream of the first heating zone is an intermediate draw roller assembly 128 comprising five rollers 128A, B, C, D and E. The rollers of the intermediate draw roller assembly 128 are rotating such as to impart to the filaments 116 a speed of about 175 m per minute. This difference in speed between the rollers of the first draw roller assembly 122 and the rollers of the intermediate draw roller assembly 128 causes the filament 116 to stretch and consequently effects a reduction in the width of the filament 116. None of the rollers 128A to E are heated or cooled.

A second heating zone 130 is arranged adjacent, and downstream of the intermediate draw roller assembly 128. The second heating zone 130 comprises an upwardly convex heating plate 132 across which the filaments 116 pass. The heating plate 132 is heated to a temperature of about 150° C.

A second draw roller assembly 134 is provided downstream of the second heating zone 130 and adjacent thereto. The second draw roller assembly 134 comprises five rollers 134A to 134E. The roller 134E which is furthest downstream of the rollers of the second draw roller assembly 134, and the roller 134D immediately upstream of the roller 134E, are cooled to a temperature of about 11–12° C. The rollers of the second draw roller assembly 134 are rotating such as to impart to the filaments 116 a speed of about 158 m per minute. The difference in speed between the rollers of the second draw roller assembly 134 and the intermediate draw roller assembly 128 and the passage of the filaments 116 across the heating zone 130 results in the relaxation of the filaments 116 to ensure there is no tension therein.

The cooling of the filaments 116 by the rollers 134D and E results in filaments that can be handled and spooled for storage.

After the second draw roller assembly 134, the filaments 116 pass to spooling means 136, known in the art at which each filament 116 are spooled into a respective individual bobbin 138 for storage.

With a polypropylene stating material 66/34LD at 59–60% wt/wt, ADFLEX at 39–40% wt/wt and $TiO_2$ colourant at 1% wt/wt the apparatus described above results in a yarn having the following properties.

| | |
|---|---|
| Width: | 0.6 mm, 1.1 mm or 1.5 mm (depending upon the distance from the die head to the water bath) |
| Decitex: | 550–1000 |
| Tensile Strength | 15–25 N |

Referring to FIG. 3, there is shown a third embodiment of the apparatus which comprises all the features of the apparatus shown in FIG. 2 and these have been designated with the same reference numerals.

In addition, the apparatus shown in FIG. 3 also includes flattening means 140 comprising a pair 142 of opposed rollers 144, 146, between which the filaments 116 passes. The surfaces of the rollers 144, 146 are spaced from each other at the point at which the filaments 116 passes therebetween by a distance sufficient to flatten the filaments 116 from a thickness of substantially 0.095 mm, to a thickness of between substantially 0.05 mm and substantially 0.075 mm.

The flattening of the filaments 116 by the flattening means 140 bilaterally orient the molecules in the filaments 116 thereby increasing the lateral strength of the filaments 116.

It will be realised that the operating conditions, extrusion dimensions etc. for all the embodiments can be amended to form polypropylene/polyethylene yarns tapes or sheets, or flosses, the characteristics of which approximate to those of equivalent PTFE products.

Whilst endeavouring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

What is claimed is:

1. A method of converting a plastics material into a dental floss, comprising heating the plastics material to melt it, passing the melted material through an extrusion die to form an extruded filament, passing the extruded filament through a plurality of draw roller assemblies, elevating the temperature of the filament at at least one of the assemblies, and thereafter cooling the filament wherein the dental floss constitutes the filament, and the filament has a width in the range of 0.6 to 1.5 mm.

2. A method according to claim 1 comprising passing the extruded filament through a draw roller assembly while elevating the temperature of the filament.

3. A method according to claim 2 wherein the filament is heated after exiting from the draw roller assembly.

4. A method according to claim 1 wherein the plastics material is selected from the group comprising polyalkenes.

5. A method according to claim 1 wherein the plastics material is polyethylene.

6. A method of converting a plastics material into a dental floss, comprising heating the material to melt it, pumping melted material through an extrusion die to form an extruded filament, cooling the extruded filament, passing the extruded filament through a first draw roller assembly while elevating the temperature of the filament, heating the filament in a heating zone as it exits from the first draw roller assembly and, thereafter, passing the filament through a second draw roller assembly operating at a different linear speed to the first draw roller assembly and spooling the filament exiting the second draw roller assembly, wherein the dental floss constitutes the filament and the filament has a width in the range of 0.6 to 1.5 mm.

7. A method according to claim 6, wherein the plastics material is selected from the group comprising polyalkenes.

8. A method according to claim 6 wherein the plastics material comprises one or more polyalkenes formed from one or more of $C_2$–$C_3$ alkenes.

9. A method according to claim 8 wherein the plastics materials is polyethylene or polypropylene, a blend of polyethylene and polypropylene, or a co-polymer of ethylene and propylene.

10. A method according to claim 9 wherein where the plastics material is a co-polymer of ethylene and propylene, the material may comprise from 0 to 100% wt/wt of said co-polymer, preferably from 0 to 60%, and more preferably from 0 to 40% of said co-polymer.

11. A method according to claim 6 wherein the material further includes polytetrafluoroethylene (PTFE).

12. A method according to claim 11 wherein the material includes PTFE in an amount of 5 to 10% wt/wt.

13. A method according to claim 6 wherein the material comprises a rubberising product comprising a propylene polymer with ethene.

14. A method according to claim 13 wherein the material comprises from 0 to 100% wt/wt of said product.

15. A method according to claim 6 wherein the material includes an ethylene vinyl acetate polymer.

16. A method according to claim 15 wherein the ethylene vinyl acetate polymer is a co-polymer, the co-polymer including a vinyl acetate in amount of 7 to 18% w/w of the co-polymer.

17. A method according to claim 15 wherein the material includes from 0 to 100% wt/wt of said ethylene vinyl acetate polymer.

18. A method according to claim 6 wherein silica is added to the plastics material.

19. A method according to claim 18, wherein the silica is added to the material in an amount of 1% to 5% wt/wt.

20. A method according to claim 6 wherein the rollers in the first heated draw roller assembly are rotating such as to impart to the filament a speed which lies within the range 0–200 m per minute.

21. A method according to claim 6 wherein the temperature of the rollers in the first heated draw roller assembly of the first embodiment lies within the range 0–200° C.

22. A method according to claim 6 wherein the temperature in the heating zone at the exit from the first draw roller assembly lies within the range 0–200° C.

23. A method according to claim 6 wherein the second draw roller assembly is heated to a temperature within the range 0–200° C.

24. A method according to claim 6 wherein the rollers of the second heated draw roller assembly of the first embodiment are rotating such as to impart to the filament a speed which lies within the range 0–1000 m per minute.

25. A method according to claim 6 wherein the filament is passed through an intermediate draw roller assembly arranged downstream of the first draw roller assembly and upstream of the second draw roller assembly.

26. A method according to claim 25 wherein the extruded filament is further heated in a second heating zone as the filament exits the intermediate draw roller assembly, the filament remaining substantially unheated as it passes through the intermediate draw roller assembly.

27. A method according to claim 6 wherein the rollers in the first draw roller assembly are rotating such as to impart to the filament a speed which lies within the range of 16–50 m per minute.

28. A method according to claim 27 wherein the first draw roller assembly comprises a plurality of rollers.

29. A method according to claim 28 wherein the temperature of at least one of the rollers in the first draw roller assembly of the second embodiment lies in the range of 50–100° C.

30. A method according to claim 29 wherein the roller of the first draw roller assembly arranged furthest downstream thereof is heated, and the roller immediately upstream of said furthest downstream roller is also heated.

31. A method according to claim 27 wherein the temperature of the first mentioned heating zone at the exit from the first draw roller assembly of the second embodiment lies in the range of 100–135° C.

32. A method according to claim 25 wherein the temperature of the second heating zone at the exit from the intermediate draw roller assembly lies in the range of 100–150° C.

33. A method according to claim 25 wherein the intermediate draw roller assembly comprises a plurality of rollers.

34. A method according to claim 33 wherein the rollers in the intermediate draw roller assembly are rotating such as to impart to the filament a speed which lies in the range 150–250 m per minute.

35. A method according to claim 6 wherein the second draw roller assembly comprise a plurality of rollers.

36. A method according to claim 35 wherein the rollers in the second draw roller assembly are rotating such as to impart to the filament a speed which lies in the range 100–250 m per minute.

37. A method according to claim 35 wherein the extruded filament is cooled as it passes through the second draw roller assembly of the second embodiment.

38. A method according to claim 37 wherein at least one of the rollers of the second draw roller assembly is at a temperature in the range of 5–15° C.

39. A method according to claim 35 wherein the roller of the second draw roller assembly arranged furthest downstream thereof is cooled, and the roller immediately upstream of said furthest downstream roller is also cooled.

40. A method according to claim 6 wherein the filament is extruded in a generally downward direction from the extruder, and the extruded filament is cooled in a water bath, the temperature of the water in the bath is controlled, the distance of the water bath from the extruder being adjustable to regulate the cross-section of the extruded filament.

41. A method according to claim 40 wherein the temperature of the melted granules lies in the range 200–300° C., and the extruder pressure lies within the range 600–1400 psi, the speed of the metering pump feeding the molten granules to the extrusion die being 1–18 revs per minute.

42. A method according to claim 40 wherein when a dental floss is formed, the distance between the extrusion die and the water level lies within the range 2 to 15 mm, and the depth of the water within the cooling bath lies within the range 0.1 and 50 cm.

* * * * *